United States Patent [19]

Pearson

[11] 4,382,685

[45] May 10, 1983

[54] METHOD AND APPARATUS FOR STIRRING PARTICLES IN SUSPENSION SUCH AS MICROCARRIERS FOR ANCHORAGE-DEPENDENT LIVING CELLS IN A LIQUID CULTURE MEDIUM

[75] Inventor: James M. Pearson, Great Shelford, England

[73] Assignee: Techne (Cambridge) Limited, Cambridge, England

[21] Appl. No.: 277,403

[22] Filed: Jun. 25, 1981

Related U.S. Application Data

[63] Continuation-in-part of Ser. No. 169,316, Jul. 16, 1980, abandoned.

[30] Foreign Application Priority Data

Jul. 17, 1979 [GB] United Kingdom ................. 7924810
Jan. 12, 1981 [EP] European Pat. Off. ......... 81300116.1
May 6, 1981 [EP] European Pat. Off. ......... 81301996.5

[51] Int. Cl.³ .............................................. B01F 3/08
[52] U.S. Cl. .................................... 366/241; 366/242; 366/306; 366/348; 366/349; 422/99; 422/228; 435/316
[58] Field of Search ............... 366/348, 602, 316, 274, 366/273, 242, 241, 287, 288, 276, 277, 278, 349, 306, 307, 243; 435/315, 316; 422/50, 99, 225, 228

[56] References Cited

U.S. PATENT DOCUMENTS

| | | | |
|---|---|---|---|
| 235,505 | 12/1880 | Buck | 366/602 |
| 1,308,038 | 7/1919 | Burnett | 366/602 |
| 1,898,094 | 2/1933 | Nies | 366/602 |
| 2,932,493 | 4/1960 | Jacobs | 366/274 |
| 3,245,665 | 4/1966 | Steel | 366/273 |
| 3,572,651 | 3/1971 | Harker | 435/316 |
| 3,576,168 | 4/1971 | Thylstrup | 366/98 |
| 3,854,704 | 12/1974 | Balas | 366/274 |
| 3,900,186 | 8/1975 | Balas | 366/242 |

FOREIGN PATENT DOCUMENTS

953338 1/1956 Fed. Rep. of Germany ...... 366/288

*Primary Examiner*—Robert W. Jenkins
*Attorney, Agent, or Firm*—Irvin A. Lavine

[57] ABSTRACT

Stirring apparatus for stirring particles in a liquid medium comprising a cylindrical stirring vessel having a stirring rod extending within the vessel to stir its contents. The rod has a bulbous tip which describes an orbital path in the vessel to sweep out an annular trough or channel formed in the bottom of the vessel. The annular trough or channel is contoured in section to follow the flow lines set up in the medium by secondary motion stirring effects. In this way accumulation of particles due to the secondary motion, which would otherwise occur at the corners and center of the bottom of the vessel, is avoided. The apparatus is advantageously useful in cell culture research particularly for stirring microcarriers in a liquid culture medium because it becomes possible to maintain the microcarriers in uniform suspension at lower stirring speeds than heretofore possible thus avoiding damage to the growing cells and improving overall cell yield.

34 Claims, 9 Drawing Figures

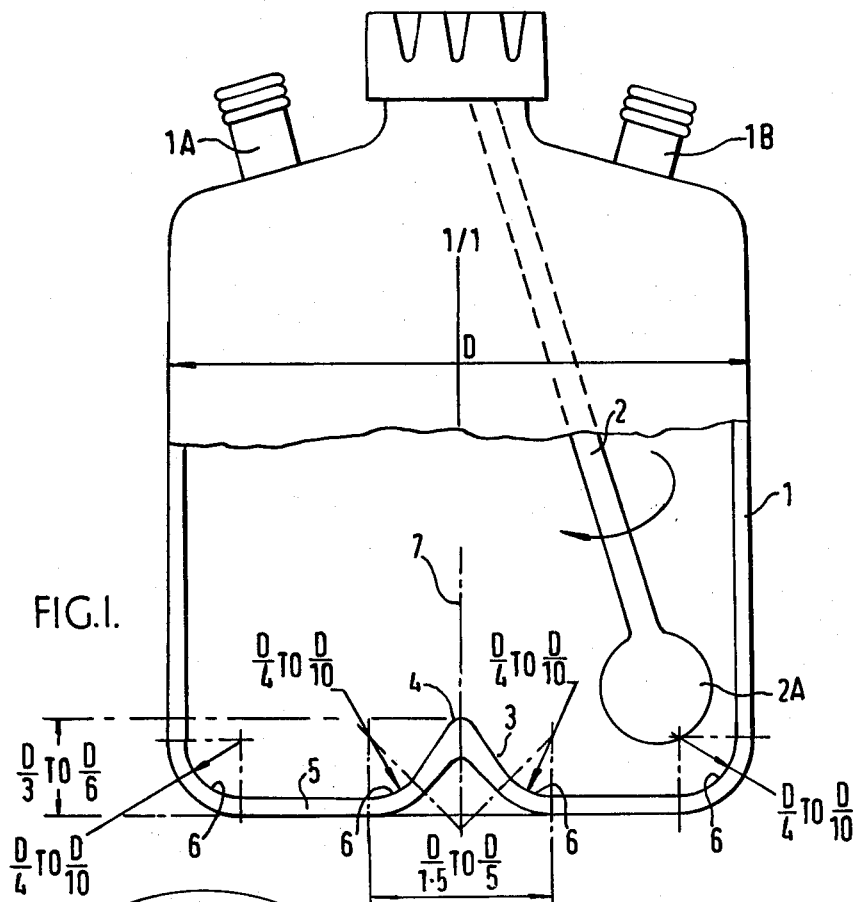
FIG. 1.
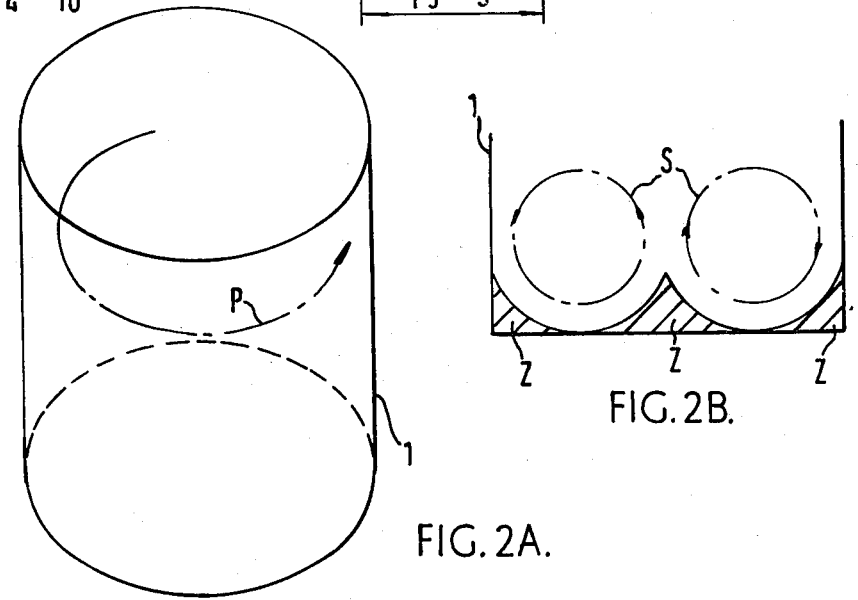
FIG. 2A.
FIG. 2B.

METHOD AND APPARATUS FOR STIRRING PARTICLES IN SUSPENSION SUCH AS MICROCARRIERS FOR ANCHORAGE-DEPENDENT LIVING CELLS IN A LIQUID CULTURE MEDIUM

CROSS REFERENCE TO RELATED APPLICATION

This application is a Continuation-In-Part of copending application Ser. No. 169,316, filed July 16, 1980 for Method and Apparatus for Stirring Particles in Suspension Such as Microcarriers for Anchorage-Dependent Living Cells in a Liquid Culture Medium, now abandoned.

FIELD OF THE INVENTION

The present invention relates to a method and apparatus for stirring particles in suspension and particularly for stirring microcarriers or beads within a liquid culture suspension to enable the growth of anchorage-dependent living cells thereon.

BACKGROUND OF THE INVENTION

The growth of living cells in a stirred liquid culture medium is well established and is important both in the research and industrial fields.

Some cell types can be grown in a stirred suspension culture without the need for the presence of an attachment surface. However, certain cell types exist which can grow only in the suspension by being termed anchorage-dependent.

In recent years methods for growing anchorage-dependent cells in suspension cultures have been developed using microcarriers, see for example U.S. Pat. No. 4,036,693. Thus use of such microcarriers is more economic relative to other known methods as it provides a large surface area for growth in relation to the volume of culture.

Normal methods for cell growth in a liquid culture medium containing microcarriers involve the necessity to maintain the microcarriers in uniform suspension while avoiding damage to growing anchorage-dependent cells.

One accepted method of stirring cell cultures has been a horizontally revolving permanent magnet either suspended by some form of bearing or as a free component allowed to find its own position in a flat bottomed culture flask. One such device is described in U.S. Pat. No. 3,572,651. Such devices are, however, not satisfactory for stirring microcarrier cultures as their minimum threshold speed is high enough to cause damage to the cells and vortices and stagnant zones are created within the stirred medium. In particular a point of stagnation develops immediately below the axis of rotation of the magnet leading to conditions of uncontrolled stirring within the culture medium and consequent non-uniformity of suspension of the microcarriers. Moreover the amount of heat generated by the motor driving the magnet is so great as to render the equipment unsuitable for use in an incubator without employing refrigeration.

A superior type of stirrer for microcarriers suspended in a liquid culture medium which obviates this problem, is disclosed in U.K. Pat. No. 1,485,741. Such a stirrer is basically comprised of a stirring rod for immersion in a liquid to be stirred contained in a flat bottomed cylindrical culture flask, the stirring rod being provided with means for imparting to it an oscillatory pivotal motion such that the end of the rod describes an orbital path within the culture flask.

One disadvantage of this type of stirrer, as with any stirrer designed to impart a rotational primary movement to a culture liquid within a flat bottomed cylindrical vessel, is that due to the effects of secondary motion within the liquid an accumulation of suspension particles occurs at the outer perimeter and the centre of the bottom of the culture vessel.

The explanation for this accumulation is well known. For example reference may be made to "The cause and formation of meanders in the course of rivers" and the so called "Beers Law" from "Ideas & Opinions" by Albert Einstein (Alvin & Redway Ltd, 1954).

In brief, the rotation of the liquid medium during the stirring action, which may be termed the primary motion of circulation, causes a centrifugal force to act on it. At the walls of the stirring vessel the liquid is restrained by friction, so that the angular velocity at which it circulates is less at the walls than in other places near the centre. In particular the angular velocity of circulation of the liquid medium, and hence the centrifugal force will be smaller near the bottom of the vessel than higher up.

The net result will be a vertical circulating movement or secondary circulating motion as opposed to the horizontal or primary circulating motion, of the liquid medium in the vessel. The suspension particles are swept by the secondary motion into the centre and corners of the bottom of the vessel, which effectively form stagnant zones during stirring within the vessel, and accumulate there with time.

SUMMARY OF THE INVENTION

The present invention provides a method and apparatus for stirring particles in suspension, particularly microcarriers in a liquid culture medium, which obviates the risk of accumulation of the microcarriers at the centre or corner of the stirring vessel by secondary motion. Damage to the growing cells is avoided because uniform suspension can be achieved at much gentler stirring speeds thus producing improved cell growth and yield in contrast with the prior art.

According to the invention there is provided apparatus for stirring particles in a liquid medium comprising a stirring vessel, an elongate stirrer extending within the vessel to stir its contents, characterised in that the vessel is shaped to deter the accumulation of particles at the bottom of the vessel caused by secondary motion stirring effects within the vessel.

The principle advantage of the stirring apparatus according to the invention is that during stirring the dead or stagnant zones at the bottom of the vessel set up by secondary motion effects in the stirred medium are deterred from forming thereby preventing the accumulation of particles in these zones. In this way it becomes possible to stir at much lower speeds than heretofore possible while still maintaining the particles in uniform suspension.

This result is of considerable importance in cell growth research employing stirred microcarriers in liquid culture mediums, because the lower stirring speeds, coupled with better uniformity of suspension of the microcarriers, mitigate the attendant possibility of damage to the growing cells, in all giving much improved cell growth and yield.

Other features and advantages of the present invention will become apparent from the description that follows.

BRIEF DESCRIPTION OF THE DRAWINGS

An embodiment of the invention will now be described by way of example with reference to the accompanying drawings wherein:

FIG. 1 is a part cross-sectional view of stirring apparatus for stirring particles in a liquid suspension in accordance with the present invention;

FIGS. 2A and 2B are illustrative of the two types of circulating motion which are set up in a liquid being stirred in the stirring vessel of the apparatus shown in FIG. 1;

BEST MODES FOR CARRYING OUT THE INVENTION

Figure 3:
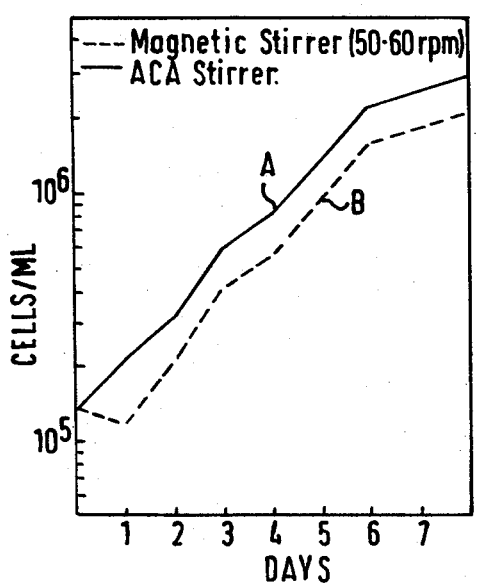
FIG. 3 is a graphical illustration showing curves of the cell yield rate achieved with apparatus according to an embodiment of the present invention compared with that achieved using the prior art magnetic spinner stirring apparatus.

A cylindrical stirring vessel 1 having a diameter D, for use in stirring microcarriers in a liquid culture medium is shown in FIG. 1. The vessel 1 is provided with ports 1A and 1B giving access to the culture medium for sampling and control of atmosphere. A stirrer rod 2 preferably made of a moulded polypropylene and having a spherical tip 2A, is shown mounted in the vessel 1 for stirring its contents, the stirrer rod being adapted, by means (not shown) to be moved such that its end describes an orbital path within the vessel, the stirring action closely resembling that of an ordinary hand-held stirring rod.

The bottom of the cylindrical vessel has an upstanding conical portion 3 which tapers to a rounded apex 4 within the interior of the flask 1, to form an interior annular trough or channel 5. The axis of the cone-shaped portion 3 lies on the central vertical axis 7 of the vessel.

The bottom corners of the trough or channel 5 are radiused at 6 as shown. The radiusing however may be continuous in the sense that the trough or channel 5 is formed by being wholly radiused between the interior surface of the conical portion 3 and the wall of the vessel.

The radiused dimensions of the trough or channel 5 are within the range ¼ to 1/10 the diameter of the vessel 1, with the height to the apex 4 of the cone-shaped portion 3 within the range ½ to 1/6 of the diameter D, to give a base diameter of the portion 3 within the range of 1.5 to 1/5 of the diameter D of the vessel 1. The diameter of the spherical tip 2A lies in the range ½ to 1/20 the diameter D of the vessel 1.

These dimensions have been found to be preferable for preventing the accumulation of microcarriers at the bottom of the stirring vessel 1 by secondary motion effects.

The advantages of stirring microcarriers in a liquid culture medium using a vessel as just described may be illustrated with reference to FIGS. 2A and 2B.

In operation the end of the stirrer rod 2 is arranged to move around the bottom of the flask as shown with an orbital motion so that its bulbous tip 2A sweeps the annular trough or channel 5, to impart lift to the microcarriers and maintain them in uniform suspension.

The action of the stirrer rod 2 will produce, as has been described earlier, two types of circulatory motion within the vessel, namely a primary motion P producing a horizontal circulatory movement of the liquid suspension about the axis of the vessel 1, as shown in FIG. 2A, and a secondary motion S producing a further vertical circulatory movement of the liquid suspension as shown in FIG. 2B.

The secondary motion S produces stagnant zones Z at the centre and at the corners of the bottom of the stirring vessel, whereat microcarriers being stirred are prone to collect.

These stagnant zones are not permitted to form during stirring in the apparatus of FIG. 1 due to the shape imparted to the bottom of the stirring vessel 1 as described wherein the contours of the trough 5 in section conform to or substantially conform to the flow lines set up during the secondary motion S thus producing a much more effective overall stirring action for maintaining the microcarriers in uniform suspension.

Thus the microcarriers being swept to the centre and corners of the vessel bottom by the secondary motion, instead of being allowed to settle there, are immediately moved back into the stirred medium by the action of the curved surfaces of the trough or channel 5, to be thereafter maintained in suspension by both the primary and secondary motion effects.

This result means that the speed of revolution of the stirrer rod 2 may be much lower than heretofore found possible to maintain the microcarriers in suspension, and thus damage to the growing cells, which is encountered when stirring at high speeds in a flat bottomed vessel to counter secondary motion effects, is avoided.

The stirrer rod 2 is rotated within the culture medium at a rotational speed within the range 30 rpm to 80 rpm. This range has been found to ensure that on the one hand at the lower end of the range, the microcarriers are lifted into suspension, and at the higher end the growing cells are not adversely affected. However, this result has been determined during experiments with microcarriers or beads of a specific type.

Thus it may be expected that, with a stirring vessel of specific dimensions, speeds lower than 30 rpm are possible with differing microcarrier types, the overriding advantage being that notwithstanding these possible lower stirring speeds, the microcarriers once lifted into suspension, will remain there due to the shaping as described of the bottom of the stirring vessel. Additionally it is to be noted that the minimum speed for microcarrier bead suspension reduces as the size of the stirring vessel increases. With this in mind stirring speeds as low as 5 rpm or less would be sufficient to maintain the carriers in suspension with the apparatus according to the invention.

Tests have been carried out to compare the performance of the stirring apparatus according to the present invention with that of the prior art, in particular the traditionally used magnetic spinner vessel referred to earlier. In these tests the stirring apparatus of the invention employed an alternating air current stirrer to operate the stirring rod 2 of the type as disclosed in U.K. Pat. No. 1,485,741 previously referred to. In these trial summaries therefore the stirring apparatus according to an embodiment of the invention as just described with reference to FIG. 1 employing the alternating air current stirrer will be referred to as the ACA stirrer system.

The most critical test in the evaluation of microcarrier stirring equipment is its ability to allow the growth of cells on the microcarriers to high culture densities. The ACA stirrer system was tested in function tests with MRC-5 (human fibroblasts) and Vero (African Green monkey kidney) cells. Of the two types of cell, the MRC-5 cells are the more difficult to grow in all culture systems and were therefore selected for use as a sensitive indicator in most of the trials.

Standard microcarrier techniques were used. Briefly, cells were cultured in Dulbecco's modification of Eagle's medium supplemented with 10 A (v/v) foetal calf serum, 10 mM HEPES and non-essential amino acids. Cytodex 1 microcarriers were used at a concentration of 3 mg/ml. Cultures were inoculated with cells and stirred immediately in the final culture volume.

The cultures were maintained at 37° C. in a water bath and were gassed with 95% air/5% $CO_2$ at the inoculation stage and every time the culture was opened for sampling or medium changes. Apart from these moments all cultures were maintained as sealed units. The medium was changed on day 4 of each growth curve when 50% of the spent medium was replaced by fresh medium. Cultures in the ACA stirrer system were compared with those in magnetic spinner vessels containing comparable culture volumes. The stirring speed of the spinner vessel was 50–60 rpm; such speed has been previously shown to be optimal for this type of vessel. Cell number was determined by the nucleus extrustion method (Sanford et al, 1951).

Trial 1 with reference to FIG. 3

MCR-5 cells were grown in 450 ml microcarrier cultures. In FIG. 3 curve A represents the cell yield rate achieved employing the ACA stirrer system while curve B that obtained with the magnetic spinner vessel. The results shown in FIG. 3 demonstrates that the ACA stirrer system results in better cell growth and yield than the magnetic spinner vessel. The main effect of the ACA stirrer system was to allow a better plating efficiency of the MRC-5 cells under these culture conditions. The better plating efficiency was reflected by a greater proportion of confluent microcarriers after 8 days and hence a high cell yield. Final cell yield was $2.08 \times 10^6$/ml with the magnetic stirrer and $2.9 \times 10^6$/ml with the ACA stirrer. Thus the ACA stirrer gave a cell yield 40% better than the magnetic stirrer. In both cases the cells had the same maximum population doubling time.

Figure 4:
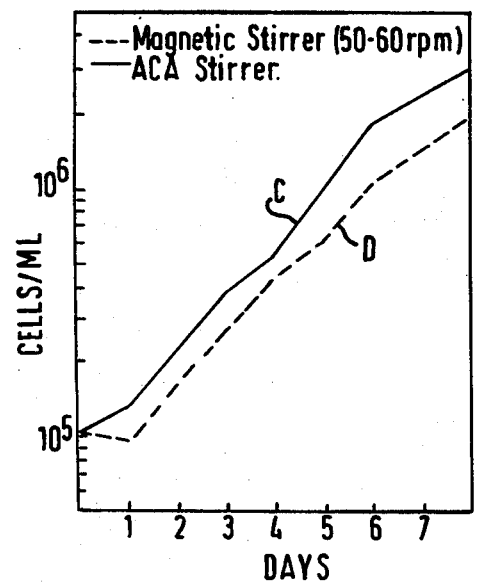
FIG. 4 is a graphical illustration similar to FIG. 3 but wherein the culture volume stirred is greater.

Trial 2 with reference to FIG. 4

MCR-5 cells were grown in microcarrier cultures of larger volume, 600 ml. This trial confirmed the results of Trial 1 (see FIG. 3) in that the ACA stirrer system proved superior to the magnetic spinner vessel, curve C representing the results with the ACA stirrer system and curve D those whem employing the magnetic spinner. In this trial, cell yield was $1.87 \times 10^6$/ml in the ACA stirrer.

Thus the ACA stirrer system gave a cell yield 57% better than the magnetic stirrer. This increase in cell yield was again due to increase in plating efficiency during the first few hours of culture.

Figure 5:
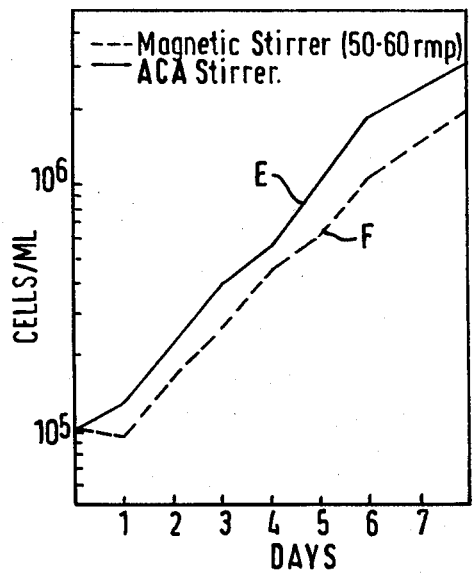
FIG. 5 is a graphical illustration similar to FIG. 3 but wherein the stirring apparatus according to an embodiment of the invention is operated at a minimum stirring speed.

Trial 3 with reference to FIG. 5

MRC-5 cells were grown in 450 ml microcarrier cultures using a lower stirring speed with the ACA stirrer system. The best result, curve E, was obtained with the slowest possible stirring speed, that is 40 rpm, presumably because of the detachment of mitotic cells from the microcarriers; curve F represents the result obtained with the magnetic stirrer. Slower stirring speeds may result in increased cell yield using the ACA stirrer system but there is the possibility that due to the poorer lift in larger culture volumes slower stirring speeds may result in suboptimal mass gas transfer and therefore suboptimal growth rates.

Figure 6:
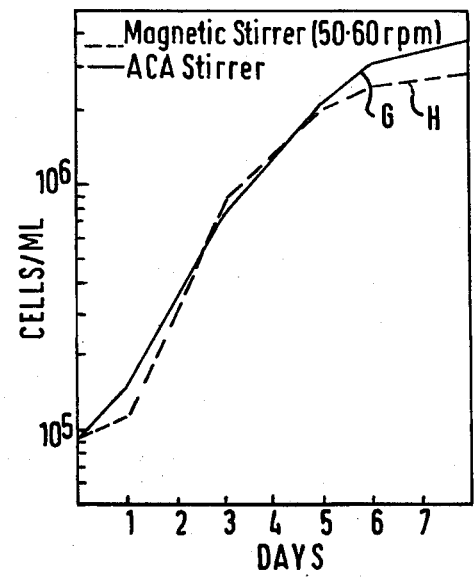
FIG. 6 is a graphical illustration similar to FIG. 3 but employing a different cell type.

Trial 4 with reference to FIG. 6

In this trial another cell type, Vero, was tested for ability to grow in the ACA stirrer system. This cell type is less sensitive than MRC-5 and has a higher intrinsic plating efficiency. It is probably for this reason that the ACA stirrer system resulted in less improvement over the magnetic spinner vessel, curve G against curve H, than was the case with the MRC-5 trials because Vero cells readily attach to the microcarriers even under the more vigorous conditions prevailing in the magnetic spinner vessel. Nevertheless the final cell yield when using the ACA stirrer system ($3.90 \times 10^6$/ml) was 37% better than that obtained with the magnetic spinner vessel ($2.87 \times 10^6$/ml).

It will be seen therefore that the ACA stirrer system resulted in cell growth and yield better than that achieved with magnetic spinner vessels. The improved cell growth and yield was most noticeable with the "more hard to grow type" MRC-5.

The apparatus of FIG. 1 employing an alternating air current to operate the stirrer rod 2 has proved to be effective for producing much improved cell yield rates compared to that possible with tradiational magnetic spinner vessels, although other methods are equally effective for example magnetic stirring where the end of the rod is constrained to move in an orbital path by magnetic attraction forces between an externally rotating magnet and a magnet housed in the tip of the rod.

Figure 7:
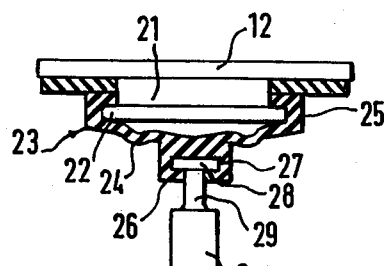
FIG. 7 is a sectional view through an embodiment of mounting means for mounting the stirrer rod in the stirring vessel of the stirring apparatus of FIG. 1.
Figure 8:
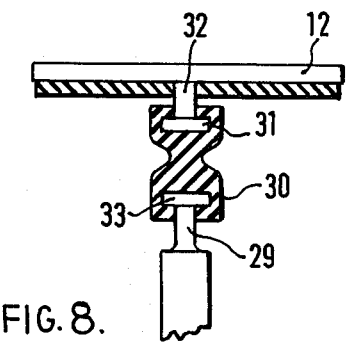
FIG. 8 is a sectional view through another embodiment of mounting means for mounting the stirrer rod in the stirring vessel of the stirring apparatus of FIG. 1.

The mounting arrangement for the rod 2 of the apparatus shown in FIG. 1 may be of the design shown in FIG. 7 or FIG. 8.

In FIG. 7 a mounting member 12 for sitting on the rim of the neck of the vessel 1, which is not shown in the drawing, is provided with an integrally formed depending projection 21 bearing an annular rim 22. The member 12 is retained on the neck of the vessel by a closure cap (not shown). A moulded flexible connection 23 having a flexible diaphragm 24, is held to the rim 22 by a cooperating annular recessed head portion 25 of the connector 23.

The diaphragm 24 is provided with a downwardly projecting integrally formed flexible support piece 26 having a recess 27 shaped to receive in gripping engagement the head 28 of a T-shaped terminating extension piece 29 of the rod 2.

The rod support embodiment of FIG. 8 employs a solid waisted flexible connection piece 30 between the rod 2 and the mounting member 12.

Each end of the waisted connecting piece 30 is provided with a T-shaped recess 31 housing in gripping engagement on the one hand a correspondingly configured T-shaped projecting member 32 of the mounting member 12, and on the other hand the T-shaped extension piece 29 of the rod 2 as shown in FIG. 7.

Both the embodiments of FIGS. 7 and 8 form a positive attachment of the rod 2 to its flexible mounting within the stirring vessel. In all cases however the arrangements shown provide a flexible mounting for the stirrer rod with no rotating bearings enabling the free end of the rod to be rotated in an orbital path while remaining irrotational around its own axis.

The stirring apparatus as described herein, when used in cell culture research, is capable of producing improved cell yield rates over the prior art, particularly the traditional magnetic spinner vessels and stirring systems employing orbiting stirrer rods in flat bottomed culture vessels.

It has additionally been shown that greater culture yields are possible with the apparatus of the present invention when intermittent short periods of agitation are introduced during the attachment phase of culture growth.

Furthermore, to minimise transient disturbances to the cultures, the stirrer rod may be caused to accelerate slowly to steady running speeds, and to decelerate slowly to stop.

The invention will now be defined in the following claims but it will be appreciated to those skilled in the art that modifications to the apparatus as described are possible which would still fall within the scope of some or all of these claims. For example although the invention has been exemplified with reference to a cylindrical vessel, nevertheless vessels of other shapes and cross-section would equally be suitable such as a conical stirring vessel.

What I claim is:

1. Apparatus for stirring micro-carriers in a liquid culture medium to allow living cells to grow thereon, comprising:
    (a) a cylindrical vessel having a bottom and side walls extending upwardly therefrom,
    (b) means for imparting to liquid culture medium in said vessel a primary generally horizontal circulatory movement about the axis of said vessel and a secondary, generally vertical circulatory movement comprising stirrer means mounted to extend into the vessel with an end adjacent to and spaced from the bottom of the vessel, and moved in an orbital path in said vessel generally concentric with said walls, and
    (c) means for causing substantially all of the liquid culture medium in the vessel to be moved by said stirrer means comprising an upstanding portion extending upwardly from the vessel bottom and spaced from said side walls thereby forming a trough in the bottom portion of said vessel.

2. Apparatus as claimed in claim 1, said last mentioned means defining an annular trough in said vessel concentric with said walls.

3. Apparatus as claimed in claim 2, wherein said annular trough is between said conical portion and the walls of said vessel, said trough being radiused at the minimum, at it's corners respectively between said wall and said base of the vessel, and between the interior surface of the conical portion and the bottom of the vessel, and at the maximum the whole extent of it's interior surface between the wall of the vessel and the interior surface of said conical portion.

4. Apparatus as claimed in claim 3, wherein the radiused dimensions of said trough are within the range ¼ to 1/10 of the diameter of the vessel, and the height of the conical portion being within the range ⅜ to 1/6 of the diameter of said vessel.

5. Apparatus as claimed in claim 1, said upstanding portion extending upwardly from the vessel bottom being conical with an apex above the bottom, and having its axis substantially coincident with the axis of the vessel walls.

6. Apparatus as claimed in claim 5, wherein the base diameter of said conical portion is within the range 1/1.5 to 1/5 the diameter of the vessel.

7. Apparatus as claimed in claim 5, wherein said conical portion has a rounded apex.

8. Apparatus as claimed in claim 1, wherein said stirrer means is an elongate rod having a bulbous tip positioned to move in said trough.

9. Apparatus as claimed in claim 8, wherein the dimensions of said bulbous tip are within the range ½ to 1/20 the diameter of the vessel.

10. Apparatus as claimed in claim 1, said stirrer means mounted with said end out of engagement with said vessel.

11. Apparatus for stirring the contents of a vessel as claimed in claim 10 further including means for supporting the stirrer within the vessel comprising a mounting member which sits on the rim of an open neck of said vessel, said mounting member having a projection depending internally of the vessel, a flexible link between the projection and the other end of said stirrer to enable the free end of the stirrer to orbit while the stirrer remains irrotational around its own axis, and a closure cap for said open neck retaining said mounting member in position on said rim.

12. Apparatus for stirring micro-carriers in a liquid culture medium to allow living cells to grow thereon comprising:
    (a) container means for a liquid comprising a bottom and wall means extending upward therefrom,
    (b) means for imparting to the liquid culture medium a primary, generally horizontal circulatory movement about the axis of the container means and a secondary, generally vertical circulatory movement, comprising stirrer means mounted to extend into the container means with an end adjacent to and spaced from the bottom, and moved in a closed path in said vessel, and
    (c) means for causing substantially all of the liquid culture medium in the container means to be moved by said stirrer means comprising an upstanding portion extending upwardly from the bottom of the container and spaced from said wall means, thereby forming a trough in the bottom portion of the container means.

13. Apparatus as defined in claim 12, said upstanding portion extending upwardly from the bottom of the container means substantially at the center thereof, and radiused corners between said bottom and said wall means and between said bottom and said upstanding portion.

14. Apparatus as claimed in claim 13, wherein said stirrer means is an elongate rod provided with a bulbous tip to move in said trough.

15. Apparatus as defined in claim 14, said portion being substantially conical.

16. Apparatus as defined in claim 15, said portion terminating in an apex.

17. Apparatus as claimed in claim 13, wherein the radiused dimensions of said trough are within the range ¼ to 1/10 of the diameter of the vessel, and the height of the conical portion being within the range ⅓ to 1/6 of the diameter of said vessel.

18. Apparatus as claimed in claim 17, wherein said stirrer means is an elongate rod having a bulbous tip positioned to move in said trough.

19. Apparatus as claimed in claim 17, wherein the dimensions of said bulbous tip are within the range ½ to 1/20 the diameter of the vessel.

20. Apparatus as defined in claim 12, said upstanding portion extending upwardly from the bottom of the container means substantially at the center thereof, said annular trough in the bottom portion of said container means wholly radiused between the interior surface of said portion and the wall means.

21. Apparatus as claimed in claim 20, wherein said stirrer means is an elongate rod provided with a bulbous tip to move in said trough.

22. Apparatus as defined in claim 21, said portion being substantially conical.

23. Apparatus as defined in claim 22, said portion terminating in an apex.

24. Apparatus as claimed in claim 20, wherein the radiused dimensions of said trough are within the range ¼ to 1/10 of the diameter of the vessel, and the height of the conical portion being within the range ⅓ to 1/6 of the diameter of said vessel.

25. Apparatus as claimed in claim 24, wherein said stirrer means is an elongate rod having a bulbous tip positioned to move in said trough.

26. Apparatus as claimed in claim 25, wherein the dimensions of said bulbous tip are within the range ½ to 1/20 the diameter of the vessel.

27. A method of stirring a liquid culture medium comprising providing a stirring vessel with provision for blocking off the corners and centre of the base of the vessel to provide an annular trough therein shaped to prevent accumulation of particles under the action of secondary motion stirring effects within the vessel, adding to the vessel liquid culture medium, introducing an elongate stirrer into said medium with it's free end spaced from the bottom of the vessel, and stirring the medium by imparting to the stirrer an orbital path with the free end moving in the trough thereby to impel the medium to circulate in the stirring vessel without accumulation.

28. A method as claimed in claim 27, wherein the medium is stirred at a rotational speed within the range 30 rpm to 70 rpm.

29. A method as claimed in claim 27, wherein said stirrer free end is moved in an orbital path out of contact with said vessel.

30. The method of claim 27, wherein the step of providing a stirring vessel comprises providing a stirring vessel with an annular trough.

31. The method as claimed in claim 27, wherein there is added to the vessel a predetermined mixture of microcarriers and said liquid culture medium, wherein the stirring is of the mixture of the liquid culture medium and microcarriers, and wherein the medium and the microcarriers are impelled to circulate in the stirring vessel without accumulation of the microcarriers.

32. A method is claimed in claim 27, said step of stirring said medium comprising intermittent stirring.

33. A method as claimed in claim 32, wherein the stirrer is accelerated slowly from rest to achieve a desired steady state stirring speed, and then decelerated slowly to zero after a predetermined time of stirring at said steady state speed.

34. A method as claimed in claim 27, wherein the stirrer is accelerated slowly from rest to achieve a desired steady state stirring speed, and then decelerated slowly to zero after a predetermined time of stirring at said steady state speed.

* * * * *